United States Patent [19]

Michniak

[11] 4,067,913
[45] Jan. 10, 1978

[54] PROCESS FOR THE PRODUCTION OF 2,5-DICHLORO-4-BROMOPHENOL

[75] Inventor: John Michniak, Bellwood, Ill.

[73] Assignee: Velsicol Chemical Corporation, Chicago, Ill.

[21] Appl. No.: 520,326

[22] Filed: Nov. 4, 1974

Related U.S. Application Data

[63] Continuation-in-part of Ser. No. 236,452, March 20, 1972, abandoned.

[51] Int. Cl.$^2$ ............................................. C07C 39/30
[52] U.S. Cl. .............................. 260/623 H; 260/629; 260/623 R
[58] Field of Search ................ 260/623 R, 623 H, 629

[56] References Cited

U.S. PATENT DOCUMENTS

| | | | |
|---|---|---|---|
| 3,012,035 | 12/1961 | Knowles et al. | 260/256.4 |
| 3,412,145 | 11/1968 | Hanna | 260/623 R |
| 3,449,443 | 6/1969 | Dietzler et al. | 260/623 H |
| 3,726,929 | 4/1973 | Payne et al. | 260/623 R |
| 3,728,403 | 4/1973 | Ross | 260/623 H |

*Primary Examiner*—James O. Thomas, Jr.
*Assistant Examiner*—W. B. Lone
*Attorney, Agent, or Firm*—Robert J. Schwarz; Dietmar H. Olesch

[57] ABSTRACT

This invention discloses a process for the preparation of 2,5-dichloro-4-bromophenol which comprises reacting a mixture of 2,5-dichlorophenol and 2,4-dichlorophenol with about 0.9 to about 1.2 molar amounts of bromine per mole of 2,5-dichlorophenol and thereafter recovering the 2,5-dichloro-4-bromophenol.

17 Claims, No Drawings

PROCESS FOR THE PRODUCTION OF 2,5-DICHLORO-4-BROMOPHENOL

This application is a continuation-in-part of my copending application Ser. No. 236,452, filed Mar. 20, 1972 now abandoned.

This invention relates to a process for the preparation of 2,5-dichloro-4-bromophenol and more particularly relates to a process for preparing said compound from an isomeric mixture of dichlorophenols by direct bromination without requiring a difficult separation of isomeric products.

The compound 2,5-dichloro-4-bromophenol is a valuable chemical useful as an intermediate for preparing certain insecticides. Heretofore this compound was prepared by brominating relatively pure 2,5-dichlorophenol. The compound 2,5-dichlorophenol, however, is difficult to obtain in substantially pure form since it is prepared from 1,2,4-trichlorobenzene by reaction with an alkali metal hydroxide which results in a product consisting of an isomeric mixture of 2,4-, 2,5- and 3,4-dichlorophenol. The 2,5-dichlorophenol is difficult to separate from this mixture due to the similarity of the vapor pressure curves of the 2,5- and 2,4-dichlorophenol. For example, the boiling points at atmospheric pressure of the 2,5- and 2,4- isomers are about 210° C. and 212° C., respectively. To separate a mixture of these isomers by distillation requires a fractionation column having in excess of 300 theoretical plates.

The 3,4-dichlorophenol surprisingly has a much higher boiling point than the other mentioned isomers and can, therefore, be separated therefrom by distillation procedures utilizing fractionation columns of conventional capacity.

It has now been found that when a mixture of 2,5-dichlorophenol and 2,4-dichlorophenol is subjected to bromination under certain reaction conditions the 2,5-dichlorophenol brominates selectively to the exclusion of the 2,4- isomer to form 2,5-dichloro-4-bromophenol. The unreacted 2,4-dichlorophenol can then be readily separated from the desired 2,5-dichloro-4-bromophenol by standard distillation procedures since these two materials now have a substantial difference in boiling points.

Thus, one embodiment of the present invention resides in a process for the preparation of 2,5-dichloro-4-bromophenol which comprises reacting a mixture comprising 2,5-dichlorophenol and 2,4-dichlorophenol with about 0.9 to about 1.2 molar amounts of bromine per mole of 2,5-dichlorophenol, and thereafter recovering the 2,5-dichloro-4-bromophenol.

Another embodiment of the present invention resides in a process for preparing 2,5-dichloro-4-bromophenol from a mixture of 2,5-, 2,4-, and 3,4-dichlorophenols, such as is obtained upon the acidification of the reaction product 1,2,4-trichlorobenzene with an alkali metal hydroxide, wherein the 3,4-dichlorophenol is first removed from the remaining isomers by disillation and the remaining mixture of 2,5- and 2,4-dichlorophenol is subjected to bromination as described above.

A further embodiment of this invention comprises a process for the preparation of 2,5-dichloro-4-bromophenol which comprises reacting a molar amount of 1,2,4-trichlorobenzene with at least two molar amounts of an alkali metal hydroxide in an inert organic reaction medium at a temperature of from about 300° F. to 450° F. to form a mixture of the alkali metal 2,5-, 2,4-, and 3,4-dichlorophenolates; acidifying said alkali metal phenolates to form the free phenols; separating the 3,4-dichlorophenol from the remaining isomers by distillation to form a mixture of 2,5- and 2,4- dichlorophenols; reacting said mixture of 2,5- and 2,4- dichlorophenols with about 0.9 to about 1.2 molar amounts of bromine per mole of 2,5-dichlorophenol; and thereafter recovering the 2,5-dichloro-4-bromophenol.

Additional embodiments of this invention will become apparent from the ensuing and more detailed description of the process.

As previously indicated, the bromination of a mixture of 2,5- and 2,4- dichlorophenols proceeds selectively to form only the brominated 2,5-dichlorophenol to the exclusion of the 2,4-isomer. This bromination can be effected by various means. For example, the mixture can be reacted with about 0.9 to about 1.2 moles of bromine per mole of 2,5-dichlorophenol in a glacial acetic acid reaction medium at a temperature of below about 40° C.

To carry out this reaction, the phenol mixture, which can contain the 2,5- and 2,4- dichlorophenols in any desired proportion and the glacial acetic acid can be charged into a conventional reaction vessel which is preferably shielded from actinic radiation and which is equipped with cooling and stirring means and a gas venting tube connected to a gas trap. The mixture is then adjusted to a desired temperature between about 0° C. and about 40° C., and preferably to a temperature of from about 5° C. to about 30° C., and bromine is slowly added thereto with stirring. The temperature of the reaction mixture is maintained below about 40° C. and preferably between about 5° C. and 30° C. during the bromine addition. Upon completion of the addition, stirring can be continued for a period of about ½ to about 4 hours to ensure completion of the reaction.

While as stated, the present process may be performed with a mixture of the 2,5- and 2,4-dichlophenols in any desired proportion, normally this mixture will contain a minimum of about 55% by weight of 2,5-dichlorophenol. The mixture can contain as much of this isomer above 55 percent by weight as is produced by its manufacturing process although as a practical matter there is little reason for using the present process should the mixture contain more than about 98 percent by weight of the 2,5-dichlorophenol.

The above-described bromination while very effective utilizes only one-half of the bromine for substitution onto the benzene ring. The remainder of the bromine forms hydrogen bromide which is not utilized in the reaction. For a more effective bromine utilization a process can be utilized wherein the mixture of 2,5- and 2,4-dichlorophenol is first reacted with about 0.45 to about 0.6 molar amounts of bromine per mole of 2,5-dichlorophenol and then with about 0.45 to about 0.6 molar amounts of chlorine per mole of original 2,5-dichlorophenol provided that the moles of chlorine do not exceed the moles of bromine. In this procedure all of the bromine is utilized for substitution onto the benzene ring and hydrogen chloride is formed in place of hydrogen bromide as the side product.

This mixed bromine chlorine reaction can be carried out in a manner similar to the reaction utilizing bromine alone. Thus, the dichlorophenol mixture is reacted with about 0.45 to about 0.6 moles of bromine per mole of 2,5-dichlorophenol in a glacial acetic acid reaction medium at a temperature between 0° C. and about 40° C. and the resulting mixture is then reacted with about 0.45 to about 0.6 moles of chlorine per mole of 2,5-dichlorophenol provided that the molar amount of chlorine does not exceed that of bromine at a temperature below about 40° C. A preferred temperature for effecting both the chlorine and the bromine addition ranges from about 5° C. to about 30° C. This process can be effected in conventional reaction equipment similar to that described in the previous bromination procedure.

A further bromination procedure which can be utilized is a bromination carried out in an inert organic solvent such as methanol in the presence of iodine catalyst. To effect this reaction the 2,5- and 2,4- dichlorophenol mixture is dissolved in an inert organic solvent and from about 0.5 to about 2.0 percent by weight of iodine is added thereto. The reaction mixture can then be heated to a temperature ranging from about 0° C. to about 40° C. and 0.9 to about 1.2 moles of bromine per mole of 2,5-dichlorophenol can be added thereto. The reaction mixture can then be stirred for a period of from ½ to 4 hours after the bromine addition while maintaining the temperature between about 0° C. and 40° C. After this time, further reaction can be stopped by the addition of from about 1 to about 5 percent by weight of sodium sulfite based on the weight of starting dichlorophenols. The reaction products can then be recovered upon evaporating the solvent.

The bromination in the presence of iodine catalyst can also be effected by reaction with from about 0.45 to about 0.6 moles of bromine per mole of 2,5-dichlorophenol followed by 0.45 to 0.6 moles of chlorine per mole of 2,5-dichlorophenol provided that the molar amount of chlorine does not exceed that of bromine thereby providing greater bromine efficiency.

Each of the described bromination procedures results in a product mixture containing 2,5-dichloro-4-bromophenol and unreacted 2,4-dichlorophenol as well as minor amounts of related compounds. The 2,5-dichloro-4-bromophenol can now be readily separated from this mixture by conventional distillation equipment without requiring a distillation column having an excessive number of theoretical plates. This distillation can be effected with a column of about 10 theoretical plates to obtain a product of at least 95 percent purity.

It is essential to the process of the instant invention that the starting material comprises a mixture of 2,5- and 2,4-dichlorophenol to the exclusion of the 3,4-dichlorophenol. The 3,4-isomer unlike the 2,4-isomer does brominate along with the 2,5-isomer and would form the 3.4-dichloro-6-bromophenol which is difficult to separate from the 2,5-dichloro-4-bromophenol due to the similarity of the vapor pressures of these isomers.

Suprisingly, however, it has been found that the 3,4-dichlorophenol can be readily removed from a mixture of 2,5-, 2,4, and 3,4-dichlorophenols by distillation due to a substantial difference in boiling points. At standard atmospheric pressure for example 3,4-dichlorophenol boils at 253° C. while 2,5- and 2,4- dichlorophenol each boil at 210° C. and 212° C., respectively. This distillation can be carried out in a column of about 10 theoretical plates and when a starting material mixture obtained upon the acidification of the reaction product of 1,2,4-trichlorobenzene with an alkali metal hydroxide is used a 2,5- and 2,4- dichlorophenol mixture containing from about 70 to about 90 percent by weight of 2,5-dichlorophenol and from about 10 to about 30 percent by weight of 2,4-dichlorophenol is obtained.

The preparation of the dichlorophenols from 1,2,4-trichlorobenzene is effected by reacting said chlorobenzene in an inert organic reaction medium with at least about two molar amounts of an alkali metal hydroxide such as sodium hydroxide or potassium hydroxide to form a mixture of the respective alkali metal 2,5-, 2,4- and 3,4- dichlorophenolates as the predominant products. These phenolates can then be converted to the corresponding phenols upon acidification with a suitable acid such as hydrochloric acid and the like.

This reaction can be readily carried out by charging the 1,2,4-trichlorobenzene and the inert organic solvent such as methanol or ethanol into a pressure vessel equipped with heating and stirring means. About two molar amounts or slight excess of an alkali metal hydroxide based on the trichlorobenzene is then added to the vessel with stirring. The pressure vessel is sealed and the reaction mixture is heated to a temperature of from about 150° C. to about 250° C. with stirring for a period of from about 1 to about 4 hours. After this time, the reaction mixture is cooled and the vessel vented to the atmosphere. Water in an amount sufficient to dissolve the alkali metal phenolates can then be added to the mixture resulting in the formation of an aqueous phase and an oil phase. The oil phase contains unreacted starting material and, when the reaction medium is an alkanol, alkylated phenols. The oil phase can then be removed by decantation leaving an aqueous solution of the phenolates containing methanol. The methanol can be removed from the aqueous solution by distillation. The minor residual oil left in the aqueous solution can be removed at this time by steam distillation. The aqueous solution is then acidified with a strong mineral acid such as hydrochloric acid to a pH of from about 4 to 6 to liberate the free phenols as an oil phase. This oil phase can then be decanted to yield the desired mixture of 2,5-, 2,4-, and 3,4- dichlorophenols.

The process of the present invention is illustrated in greater detail in the following examples:

EXAMPLE 1

Preparation of Dichlorophenols 1,2,4-Trichlorobenzene (181 grams; 1 mole), methanol (220 ml) and flaked sodium hydroxide (80 grams) are charged into a pressure vessel equipped with heating and stirring means. The reaction mixture is then heated with stirring at a temperature of about 185° C. for a period of about 3 hours. After this time, the reaction mixture is cooled and water (250 ml) is added thereto. The mixture is first stirred and then allowed to stand thereby forming an aqueous phase and an oil phase. The oil phase containing unreacted starting material and anisols is removed by decantation. The aqueous phase is then distilled to remove the methanol. The remaining aqueous solution is transferred into a reaction vessel equipped with a distillation head and is subjected to steam distillation to remove the residual portion of the oil phase. The remaining aqueous solution containing the sodium dichlorophenolates is acidified with hydrochloric acid to a pH of about 4 to liberate the free phenols as a separate oil phase. This oil phase is then recovered by decantation to yield the desired product consisting essentially of a mixture of 2,5-, 2,4-, and 3,4-dichlorophenols in a proportion of about 75, 15, and 8 parts by weight, respectively.

EXAMPLE 2

Separation of 3,4-Dichlorophenol

A mixture of 2,5-, 2,4-, and 3,4- dichlorophenols prepared in accordance with Example 1 is charged into a reaction vessel equipped with a distillation column of about 10 theoretical plates. The mixture is then heated to a temperature of about 180° C. under a vacuum of about 100 mm of Hg pressure and the fraction distilling over at about 140° C. is recovered to yield the desired 2,5- and 2,4-dichlorophenol product mixture in an about 80 to 20 percent by weight ratio, respectively.

EXAMPLE 3

Bromination of Dichlorophenols

A mixture of 2,5-dichlorophenol and 2,4-dichlorophenol (84.5 grams) consisting of about 84 percent by weight of 2,5-dichlorophenol and 16 percent by weight of 2,4-dichlorophenol, and glacial acetic acid (86 grams) were charged into a reaction vessel equipped with a mechanical stirrer, thermometer and addition tube. The mixture was cooled to a temperature of about 14° C. and bromine (35.3 grams) was added dropwise with stirring over a period of about 1 hour. After this time, chlorine (15.65 grams) was added to the reaction mixture with stirring over a period of about 2½ hours while the temperature of the reaction mixture was maintained at about 14° C. After this addition was completed, stirring and cooling were continued for another 2 hours. An aqueous solution of sodium sulfite (5.5 grams) was then added to the mixture to stop any further reaction. The reaction mixture was transferred into a separatory funnel and a mixture of ether (300 ml) and water (300 ml) containing sodium hydroxide (56 grams) was added thereto. The mixture was shaken forming an aqueous and oil phase. The oil phase was separated from the aqueous phase and was washed with aqueous sodium chloride. The oil phase was then separated and dried over anhydrous magnesium sulphate and stripped of ether to yield a product mixture having the following analysis by gas chromatography:

2,5-Dichlorophenol: 3.1%
2,4-Dichlorophenol: 10.6%
6-Bromo-2,4-dichlorophenol: 0.78%
6-Bromo-2,5-dichlorophenol: 2.4%
4-Bromo-2,5-dichlorophenol: 79.7%
4-Bromo-2,3-dichlorophenol: 0.76%
4,6-Dibromo-2,5-dichlorophenol: 2.5%
Unknown: 0.76%

EXAMPLE 4

Recovery of 4-Bromo-2,5-dichlorophenol

The product mixture of Example 3 is charged into a glass reaction vessel equipped with a thermometer, heating means and a distillation column having about 10 theoretical plates. The mixture is heated under a vacuum of about 80 mm of Hg and the fraction distilling over at about 184° C. to 187° C. is recovered to yield the desired product 4-bromo-2,5-dichlorophenol having at least a 95 percent by weight purity.

EXAMPLE 5

Preparation of Dichlorophenols 1,2,4-Trichlorobenzene (180 grams), ethanol (250 ml) and potassium hydroxide (120 grams) are charged into a pressure vessel equipped with heating and stirring means. The reaction mixture is then heated with stirring at a temperature of about 190° C. for a period of about 2 hours. After this time, the reaction mixture is cooled and water (250 ml) is added thereto. The mixture is first stirred and then allowed to stand thereby forming an aqueous phase and an oil phase. The oil phase containing unreacted starting material and anisols is removed by decantation. The aqueous phase is then distilled to remove the ethanol. The remaining aqueous solution is transferred into a reaction vessel equipped with a distillation head and is subjected to steam distillation to remove the residual portion of the oil phase. The remaining aqueous solution containing the potassium dichlorophenolates is acidified with hydrochloric acid to a pH of about 6 to liberate the free phenols as a separate oil phase. This oil phase is then recovered by decantation to yield the desired product consisting essentially of a mixture of 2,5-, 2,4-, and 3,4-dichlorophenols.

EXAMPLE 6

Separation of 3,4-Dichlorophenol

The mixture of 2,5, 2,4-, and 3,4-dichlorophenols prepared by the procedure described in Example 5 is charged into a reaction vessel equipped with a thermometer, heating mantle and a distillation column of about 10 theoretical plates. The mixture is then heated under a vacuum of about 100 mm of mercury and the fraction distilling over at a temperature of about 135° C. to 145° C. is recovered to yield the desired 2,5- and 2,4-dichlorophenol product mixture.

EXAMPLE 7

Bromination of Dichlorophenols

A mixture of 2,5-dichlorophenol (163 grams) and 2,4-dichlorophenol (37 grams) was charged into a glass reaction vessel equipped with a mechanical stirrer, thermometer, gas outlet tube with a water gas trap, and addition funnel. Iodine (1.0 grams) was added and the resulting mixture was heated to a temperature of about 113° C. with stirring to ensure uniform distribution of the iodine. The mixture was then cooled to a temperature of about 60° C. and bromine (168 grams) was slowly added thereto over a period of about 35 minutes. After the addition was completed, the mixture was stirred for a period of about one hour while maintaining the temperature between about 60° C and 65° C. The reaction mixture was then treated with sodium sulfite (10 grams) dissolved in water (200 ml), was cooled to room temperature and was transferred into a separatory funnel. Ether (1000 ml) and concentrated aqueous sodium chloride (400 ml) was added to the mixture. The ether phase was separated from the aqueous phase and was washed with an additional portion of concentrated aqueous sodium chloride (200 ml). The ether solution was then dried over anhydrous magnesium suphate and filtered to yield a product mixture dissolved in ether having the following analysis:

2,5-Dichlorophenol: 1.04%
2,4-Dichlorophenol: 12.3%
6-Bromo-2,4-dichlorophenol: 1.9%
6-Bromo-2,5-dichlorophenol: 4.3%
4-Bromo-2,5-dichlorophenol: 78.0%
4-Bromo-2,3-dichlorophenol: 0.13%
4,6-Dibromo-2,5-dichlorophenol: 2.4%

I claim:

1. A process for the preparation of 2,5-dichloro-4-bromophenol which comprises reacting a mixture of 2,5-dichlorophenol and 2,4-dichlorophenol with about 0.9 to about 1.2 molar amounts of bromine per mole of 2,5-dichlorophenol in a glacial acetic acid reaction medium at a temperature between about 0° C. and about 40° C., thereafter recovering the 2,5-dichloro-4-bromophenol.

2. The process of claim 1 wherein the 2,5-dichlorophenol constitutes a minimum of about 55 percent by weight of the mixture of 2,5-dichlorophenol and 2,4-dichlorophenol.

3. The process of claim 1 wherein the mixture of 2,5-dichlorophenol and 2,4-dichlorophenol comprises from about 70 to about 90 percent by weight of 2,5-dichlorophenol and from about 10 to about 30 percent by weight of 2,4-dichlorophenol.

4. The process of claim 1 wherein the reaction is carried out at a temperature of from about 5° C. to about 30° C.

5. The process of claim 1 wherein the 2,5-dichloro-4-bromophenol is recovered by distillation.

6. The process of claim 1 which comprises reacting a mixture comprising from about 70 to about 90 percent by weight of 2,5-dichlorophenol and from about 10 to about 30 percent by weight of 2,4-dichlorophenol with about 0.9 to about 1.2 molar amounts of bromine per mole of 2,5-dichlorophenol in a glacial acetic acid reaction medium and thereafter recovering the 2,5-dichloro-4-bromophenol by distillation.

7. A process for the preparation of 2,5-dichloro-4-bromophenol from a mixture of 2,5-, 2,4-, and 3,4-dichlorophenols which comprises separating the 3,4-dichlorophenol from the remaining isomers by distillation to form a mixture of 2,5- and 2,4- dichlorophenols and thereafter subjecting the mixture of 2,5- and 2,4-dichlorophenols to the process of claim 1.

8. A process for the preparation of 2,5-dichloro-4-bromophenol which comprises reacting a mixture of 2,5-dichlorophenol and 2,4-dichlorophenol with about 0.45 to about 0.6 molar amounts of bromine per mole of 2,5-dichlorophenol in a glacial acetic acid reaction medium at a temperature between about 0° C. to 40° C.; reacting the resulting mixture with about 0.45 to about 0.6 molar amounts of chlorine per mole of 2,5-dichlorophenol providing the molar amount of chlorine does not exceed that of bromine and thereafter recovering the 2,5-dichloro-4-bromophenol.

9. The process of claim 8 which comprises reacting a mixture of 2,5-dichlorophenol and 2,4-dichlorophenol with about 0.45 to about 0.6 molar amounts of bromine per mole of 2,5-dichlorophenol in a glacial acetic acid reaction medium at a temperature between about 0° C. and 40° C., reacting the resulting mixture with about 0.45 to about 0.6 molar amounts of chlorine per mole of 2,5 -dichlorophenol providing the molar amount of chlorine does not exceed that of bromine and thereafter recovering the 2,5-dichloro-4-bromophenol.

10. The process of claim 8 wherein the mixture of 2,5-dichlorophenol and 2,4-dichlorophenol comprises from about 70 to about 90 percent by weight of 2,5-dichlorophenol and from about 10 to about 30 percent by weight of 2,4-dichlorophenol.

11. The process of claim 8 wherein the reaction is carried out at a temperature of from about 5° C. to about 30° C.

12. The process of claim 8 wherein the 2,5-dichloro-4-bromophenol is recovered by distillation.

13. The process of claim 8 which comprises reacting a mixture comprising from about 70 to about 90 percent by weight of 2,5-dichlorophenol and from about 10 to about 30 percent by weight of 2,4-dichlorophenol with about 0.45 to about 0.6 molar amounts of bromine per mole of 2,5-dichlorophenol in a glacial acetic acid reaction medium at a temperature of from about 5° C. to about 30° C.; reacting the resulting mixture with about 0.45 to about 0.6 molar amounts of chlorine per mole of 2,5-dichlorophenol provided the molar amount of chlorine does not exceed that of bromine at a temperature of from about 5° C. to about 30° C., and thereafter recovering the 2,5-dichloro-4-bromophenol by distillation.

14. A process for the preparation of 2,5-dichloro-4-bromophenol from a mixture of 2,5-, 2,4-, and 3,4-dichlorophenols which comprises separating the 3,4-dichlorophenol from the remaining isomers by distillation to form a mixture of 2,5- and 2,4- dichlorophenols and thereafter subjecting the mixture of 2,5- and 2,4-dichlorophenols to the process of claim 8.

15. A process for the preparation of 4-bromo-2,5-dichlorophenol which comprises reacting a mixture of 2,5-dichlorophenol and 2,4-dichlorophenol, said mixture having at least 55 percent 2,5-dichlorophenol, with an equimolar amount of bromine in a glacial acetic acid reaction medium at a temperature of about 30° C. and thereafter recovering the 4-bromo-2,5-dichlorophenol.

16. A process for the preparation of 4-bromo-2,5-dichlorophenol which comprises reacting a mixture of 2,5-dichlorophenol and 2,4-dichlorophenol with an equimolar amount of bromine in a glacial acetic acid reaction medium at a temperature of about 30° C. and thereafter recovering the 4-bromo-2,5-dichlorophenol.

17. A process for the preparation of 4-bromo-2,5-dichlorophenol which comprises reacting a mixture of 2,5-dichlorophenol and 2,4-dichlorophenol obtained by saponifying 1,2,4-trichlorobenzene and distilling 3,4-dichlorophenol from the resulting mixture, with an equimolar amount of bromine in a glacial acetic acid reaction medium at a temperature of about 30° C. and thereafter recovering the 4-bromo-2,5-dichlorophenol.

* * * * *